(12) United States Patent
Bodner et al.

(10) Patent No.: US 11,925,804 B2
(45) Date of Patent: Mar. 12, 2024

(54) MULTI-DEVICE OBSTRUCTIVE SLEEP APNEA (OSA) TREATMENT

(71) Applicant: Medtronic Xomed, LLC, Jacksonville, FL (US)

(72) Inventors: Jeffrey P. Bodner, Plymouth, MN (US); Avram Scheiner, Vadnais Heights, MN (US); Phillip C. Falkner, Minneapolis, MN (US); James Britton Hissong, Jacksonville, FL (US); Walton W. Baxter, III, San Clemente, CA (US); Richard T. Stone, Minneapolis, MN (US); Robert T. Sandgren, Lindstrom, MN (US); Ryan B. Sefkow, Plymouth, MN (US); Adam J. Rivard, Blaine, MN (US)

(73) Assignee: Medtronic Xomed, LLC, Jacksonville, FL (US)

( * ) Notice: Subject to any disclaimer, the term of this patent is extended or adjusted under 35 U.S.C. 154(b) by 371 days.

(21) Appl. No.: 17/453,474

(22) Filed: Nov. 3, 2021

(65) Prior Publication Data
US 2023/0136535 A1     May 4, 2023

(51) Int. Cl.
*A61N 1/36*     (2006.01)
*A61N 1/05*     (2006.01)
*A61N 1/372*     (2006.01)

(52) U.S. Cl.
CPC .......... *A61N 1/3611* (2013.01); *A61N 1/0551* (2013.01); *A61N 1/3601* (2013.01); *A61N 1/36135* (2013.01); *A61N 1/37288* (2013.01)

(58) Field of Classification Search
None
See application file for complete search history.

(56) References Cited

U.S. PATENT DOCUMENTS

| 8,226,569 | B2 | 7/2012 | Sotos et al. |
| 8,744,572 | B1 | 6/2014 | Greenhut et al. |
| 9,636,511 | B2 | 5/2017 | Carney et al. |
| 9,757,560 | B2 | 9/2017 | Papay |
| 9,808,632 | B2 | 11/2017 | Reinke et al. |
| 9,849,288 | B2 | 12/2017 | Meadows et al. |

(Continued)

FOREIGN PATENT DOCUMENTS

EP     3071288 B1     11/2018

*Primary Examiner* — Jennifer Pitrak McDonald
*Assistant Examiner* — Elizabeth K So
(74) *Attorney, Agent, or Firm* — Shumaker & Sieffert, P.A.

(57) ABSTRACT

A first medical device for obstructive sleep apnea therapy includes therapy delivery circuitry coupled to a first set of electrodes implantable proximate to a first hypoglossal nerve within a tongue of the patient and configured to deliver a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and sensing circuitry coupled to the first set of electrodes and configured to receive a second electrical stimulation signal, delivered to the second hypoglossal nerve by the second medical device, that includes information that the second medical device communicates to the first medical device.

21 Claims, 6 Drawing Sheets

(56) References Cited

U.S. PATENT DOCUMENTS

| | | |
|---|---|---|
| 10,029,098 B2 | 7/2018 | Papay |
| 10,065,038 B2 | 9/2018 | Papay |
| 10,744,339 B2 | 8/2020 | Makansi |
| 11,426,201 B2 * | 8/2022 | Scheiner ................ A61B 5/686 |
| 2006/0135999 A1 | 6/2006 | Bodner et al. |
| 2014/0228905 A1 | 8/2014 | Bolea |
| 2020/0246627 A1 | 8/2020 | Bodner et al. |
| 2020/0269044 A1 | 8/2020 | Papay |
| 2020/0282215 A1 | 9/2020 | Scheiner et al. |
| 2020/0338358 A1 | 10/2020 | Makansi |
| 2020/0346016 A1 | 11/2020 | Caparso et al. |
| 2020/0346017 A1 | 11/2020 | Caparso et al. |
| 2021/0228234 A1 * | 7/2021 | Scheiner .............. A61B 5/4848 |

\* cited by examiner

MULTI-DEVICE OBSTRUCTIVE SLEEP APNEA (OSA) TREATMENT

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft palate moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to an implantable medical device (IMD) system and methods for delivering therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient (e.g., base of the tongue where the hypoglossal nerves for the protrusor muscles are located). In response to the electrical stimulation, the hypoglossal nerve(s) causes protrusor muscles (e.g., genioglossus and geniohyoid muscles) to contract and move the tongue forward, thereby opening the airway.

This disclosure describes examples in which a patient is implanted with multiple IMDs (e.g., two IMDs). The multiple IMDs together stimulate the hypoglossal nerves of the patient. For example, a first IMD may stimulate the left hypoglossal nerve, and a second IMD may stimulate the right hypoglossal nerve. In one or more examples, the multiple IMDs may communicate with one another. In accordance with one or more examples described in this disclosure, a first IMD may output a first stimulation signal that provides stimulation to the first hypoglossal nerve or the first and second hypoglossal nerves, and includes a first set of information to communicate to the second medical device. A second IMD may sense the first stimulation signal (e.g., sense at least a portion of the first stimulation signal), and retrieve the first set of information from the sensed first stimulation signal. In addition, the second IMD may output a second stimulation signal that provides stimulation to the second hypoglossal nerve or the first and second hypoglossal nerves, and includes a second set of information to communicate to the first medical device. The first IMD may sense the second stimulation signal (e.g., sense at least a portion of the second stimulation signal), and retrieve the second set of information from the sensed second stimulation signal.

In this manner, the example techniques describe using stimulation signals for at least two purposes. A first purpose is to stimulate a hypoglossal nerve, and a second purpose is to transmit information (e.g., for coordination of operation with another device).

In one example, the disclosure describes a medical device for obstructive sleep apnea therapy, wherein the medical device is a first medical device implantable within a head or neck of a patient, and wherein the first medical device comprises: therapy delivery circuitry coupled to a first set of electrodes implantable proximate to a first hypoglossal nerve within a tongue of the patient and configured to deliver a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and sensing circuitry coupled to the first set of electrodes and configured to receive a second electrical stimulation signal, delivered to the second hypoglossal nerve by the second medical device, that includes information that the second medical device communicates to the first medical device.

In one example, the disclosure describes a system for obstructive sleep apnea therapy, the system comprising: a first set of electrodes implantable proximate to a first hypoglossal nerve within a tongue of a patient; a second set of electrodes implantable proximate a second hypoglossal nerve within the tongue of the patient; a first medical device implantable within a head or neck of the patient and coupled to the first set of electrodes; and a second medical device implantable within the head or neck of the patient and coupled to the second set of electrodes, wherein the first medical device is configured to deliver an electrical stimulation signal via one or more of the first set of electrodes to the first hypoglossal nerve that causes the tongue of the patient to advance and includes information to communicate to the second medical device, and wherein the second medical device is configured to receive the information included in the electrical stimulation signal delivered by the first medical device via sensing of the electrical stimulation signal by one or more electrodes of the second set of electrodes.

In one example, the disclosure describes a method for obstructive sleep apnea treatment, the method comprising: delivering, with a first medical device that is implantable within a head or neck of a patient and coupled to a first set of electrodes implantable proximate to a first hypoglossal nerve within a tongue of the patient, a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and receiving, with the first medical device, a second electrical stimulation signal, delivered to the second hypoglossal nerve by the second medical device, that includes information that the second medical device communicates to the first medical device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
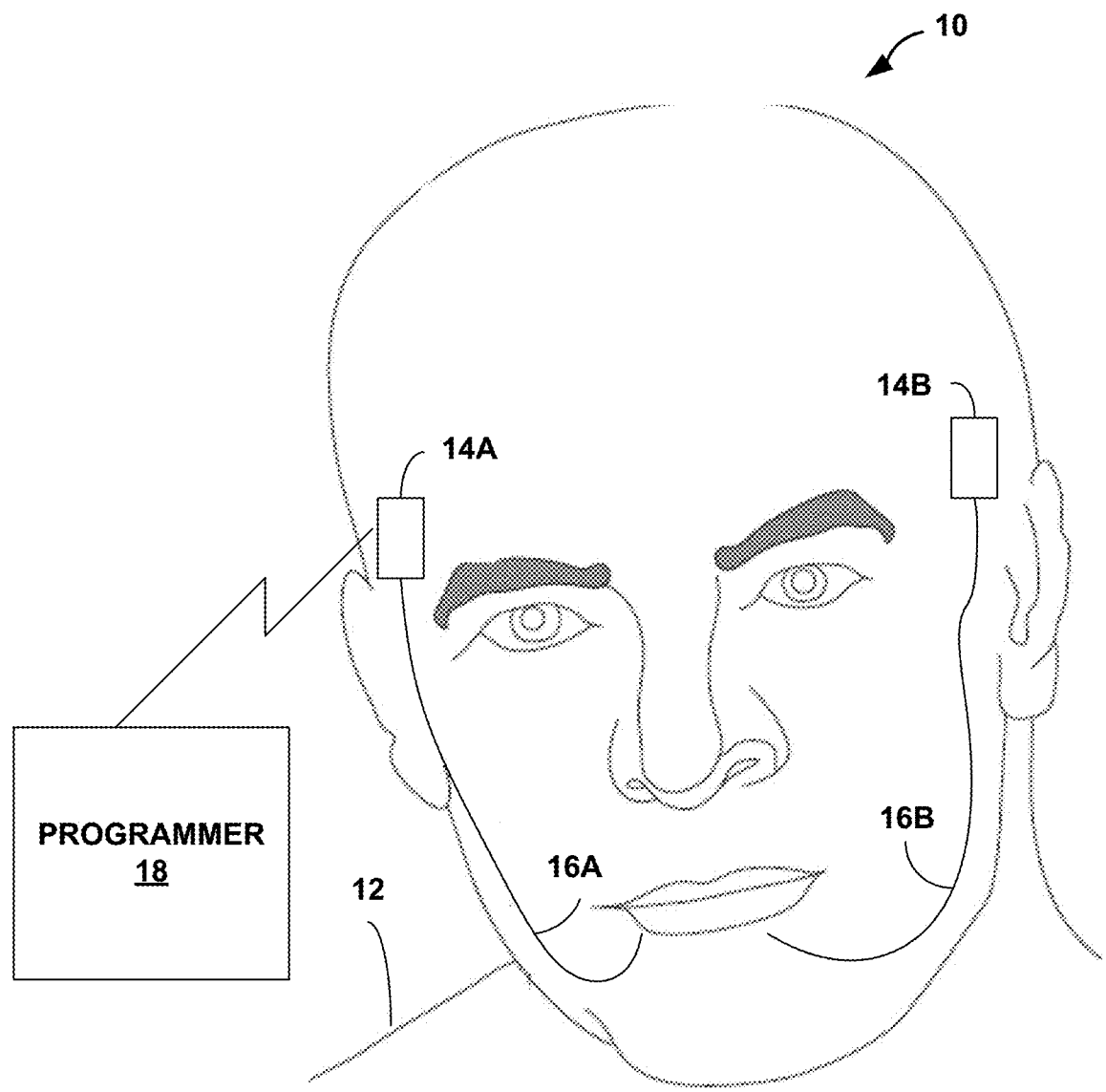
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to a non-stimulated position or a relaxed position of the tongue. In the protruded state, although possible, the tongue need not necessarily advance external to the mouth, and generally refers to a state in which the tongue is advanced forward and/or downward compared to a non-stimulated position or a relaxed position of the tongue. The protruded state is a state associated with contraction (e.g., via innervation from nerves in response to electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse or blockage of, open, or widen the upper airway of a patient to at least partially maintain or increase airflow (e.g., promote unrestricted airflow or at least reduced restriction of airflow during breathing).

The disclosure describes examples of having two or more medical devices for delivering therapy to alleviate OSA. In some examples, each of the medical devices is a small stimulator implantable in the head (e.g., behind the ear), which may provide benefits over pectoral implants due to reduction in stress on leads. However, the example techniques also include examples where the medical devices are implantable elsewhere, and have larger sizes than simulators sized to be implanted in the head.

This disclosure describes example techniques of communicating between the medical devices. For instance, each of the medical devices may be configured to stimulate one of the hypoglossal nerves in the patient (e.g., a first medical device to stimulate the left hypoglossal nerve, and a second medical device to stimulate the right hypoglossal nerve). However, it is possible that one medical device stimulates both hypoglossal nerves. In some examples, the first and second medical devices may alternate or otherwise synchronize stimulation. To synchronize stimulation, the medical devices may communicate with one another to set a schedule. There may be other reasons for the medical devices to communicate with one another, such as to set amplitude, pulse width, frequency, duration, etc. of the stimulation, and the example techniques should not be considered limited to examples of the medical devices communicating for synchronizing stimulation.

One example way in which the medical device may communicate with one another is based on the stimulation signal of a medical device providing stimulation to a hypoglossal nerve, and also including information. Another medical device may sense the stimulation signal, and retrieve the information from the stimulation signal. For instance, the stimulation signal that a first medical device outputs may be the carrier signal, and the first medical device may modulate the stimulation signal (e.g., phase, pulse-width, frequency, or amplitude modulate) to encode the information. A second medical device may sense the stimulation signal, and demodulate the stimulation signal to retrieve the information.

In some cases, the pulse width, amplitude, and/or frequency of the stimulation signal need not necessarily be extremely precise to cause the tongue to protrude (e.g., advance). Although it is possible for the tongue to protrude to extend out of the mouth, the example techniques described in this disclosure do not require the tongue to protrude so far that the tongue extends out of the mouth. In general, protruding of the tongue may be considered as the tongue advancing and opening up the airway to reduce sleep apnea events. Therefore, there may be flexibility in how much the stimulation signal can be modulated without impacting the ability of the stimulation signal to cause the tongue to advance. For instance, even if the amplitude of the phase modulation is relative high, the change in the stimulation signal may not impact the ability of the stimulation signal to cause the tongue to advance.

Because the medical devices are configured to output stimulation signals to treat OSA, utilizing the same stimulation signals for carrying information allows for communication between the medical devices without an increase in power consumption from signal transmission. For instance, it may be possible for one of the medical devices to include RF telemetry circuitry to communicate with an external programmer. However, rather than all medical devices including such RF telemetry circuitry, the medical device having the RF telemetry circuitry may communicate with the other medical devices using the stimulation signals with the embedded information that is to be communicated. In this manner, the power consumption of the medical devices that do not include the RF telemetry circuitry may be reduced.

FIG. 1 is a conceptual diagram of a medical system for delivering OSA therapy. In system 10, IMD 14A and IMD 14B (collectively referred to as IMDs 14) are implantable within patient 12. In some examples, IMDs 14 may be microstimulator devices. As one example, the size of IMDs 14 may be approximately 3 $cm^3$ (e.g., in range to 2 to 10 $cm^3$). The length may be approximately 50 mm (e.g., in range of 25 to 75 mm), and the height may be approximately 20 mm (e.g., in range of 10 to 30 mm). The dimensions of IMDs 14 is provided simply as an example, and should not be considered limiting.

In the example of FIG. 1, IMDs 14 are implanted within the head of patient 12 above or behind respective ears. For instance, IMD 14A is implanted within the head (e.g., under the skin of the head or scalp) and behind right ear of patient 12, and IMD 14B is implanted within the head and behind the left ear of patient 12. As another example, IMDs 14 may be implanted subcutaneously in the neck. IMDs 14 may be microstimulator devices. The fixation of IMDs 14 may be with tines, ridges, or bumps that hold IMDs 14 in place until scar tissue forms that further limits movement of IMDs 14. The location of IMDs 14 is provided for illustration purposes only. For instance, the small size of IMDs 14 may allow for placement on the neck or skull.

In some examples, there may be benefits in utilizing IMDs 14 having a size of a microstimulator device. For instance, as illustrated, IMD 14A is connected to lead 16A, and IMD 14B is connected to lead 16B (collectively leads 16). By having IMDs 14 implanted behind the ear, or in the neck or skull, the length of leads 16 may be smaller with reduced fatigue as compared to IMDs 14 being implanted elsewhere. Also, the effects of external signals, such as magnetic resonance imaging (MRI) scans, may be limited for small sized IMDs 14. For instance, there may be less heating of IMDs 14 from the MRI compared to larger sized IMDs. Having smaller sized IMDs 14 may also improve patient comfort and cosmesis as the small size of IMDs 14 may be less noticeable.

For ease of illustration and description, the example techniques are described with respect to IMDs 14 implanted behind respective ears of patient 12. However, the example techniques are not so limited. For instance, the example techniques are applicable to examples where there are more than two IMDs 14. The example techniques are also applicable to examples for larger sized IMDs, such as IMDs implanted within one or more pectoral region of patient 12.

Leads 16 include a flexible, elongate lead body that extends from lead proximal end (e.g., near IMDs 14) to lead distal end (e.g., within the tongue of patient 12 where prostrusor muscles are located). As illustrated in more detail in FIG. 2, distal portions of leads 16 may be implanted within the tongue of patient 12 for stimulating hypoglossal nerves of patient 12. For instance, IMDs 14 may each output a stimulation signal that respective leads 16, via respective electrodes, output to the hypoglossal nerve within the tongue of patient 12 that causes the tongue to advance forward and clear the airway.

Figure 2:
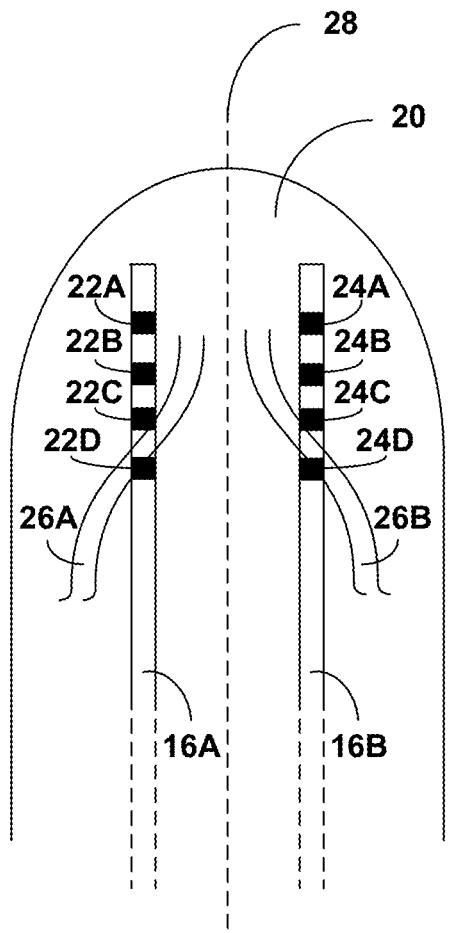
FIG. 2 is a conceptual diagram of an example of leads implanted in a tongue for delivering OSA therapy.

FIG. 2 is a conceptual diagram of an example of leads 16 implanted in tongue 20 for delivering OSA therapy. As illustrated in FIG. 2, each of leads 16 may be implanted within tongue 20 of patient 12. In some examples, leads 16 may not be implanted within the portion of tongue 20 that can be visually seen as moving when tongue 20 advances or retracts, but rather in the base of tongue 20 where the protrusor muscles are located, so as to the stimulate the hypoglossal nerve at motor end points of the hypoglossal nerve in the protrusor muscles. However, it may be possible to implant leads 16 within the portion of tongue 20 that moves. As one example, each of leads 16 may be implanted equidistant from midline 28 of tongue 20; however, leads 16 do not necessarily have to be implanted equidistance from midline 28. Also, although leads 16 are illustrated as being parallel with midline 28, the example techniques are not so limited. Example techniques to implant leads 16 in tongue 20 for delivering OSA therapy are described in U.S. Patent Publication No. 2020/0281763, the content of which related to implantation are incorporated by reference.

In some examples, leads 16 may have low elastic stiffness in tension, allowing leads 16 to absorb residual motion (e.g., motion in jaw from chewing or talking). Lead 16A may be configured to deliver stimulation signals to hypoglossal nerve 26A, and lead 16B may be configured to deliver stimulation signals to hypoglossal nerve 26B (collectively hypoglossal nerves 26). For instance, lead 16A includes electrodes 22A-22D, and lead 16B includes electrodes 24A-24D. Electrodes 22A-22D are an example of a first set of electrodes, and electrodes 24A-24D are an example of a second set of electrodes.

One or more electrodes 22A-22D of lead 16A or electrodes 24A-24D of lead 16B may be ring electrodes, segmented electrodes, partial ring electrodes, or combinations thereof, or any suitable electrode configuration. In some examples, electrodes 22A-22D or electrodes 24A-24D may be exposed coil or cable so that electrodes 22A-22D or electrodes 24A-24D are highly flexible and can bend or move as tongue 20 moves. For instance, within leads 16, there may be a coil or a cable that carries the stimulation signal from IMDs 14. Electrodes 22A-22D or electrodes 24A-24D may be formed by removing the insulation of leads 16 at specific locations to expose the coil or cable. The stimulation signals from respective IMDs 14 may then stimulate hypoglossal nerves 26 through the exposed coil or cable that form electrodes 22A-22D or electrodes 24A-24D.

Ring electrodes extend 360 degrees around the circumference of the lead body of leads 16. Segmented and partial ring electrodes each extend along an arc less than 360 degrees (e.g., 90-120 degrees) around the outer circumference of the lead body of leads 16. In this manner, multiple segmented electrodes may be disposed around the perimeter of leads 16 at the same axial position of the lead. In some examples, segmented electrodes may be useful for targeting different fibers of the same or different nerves 26 at respective circumferential positions with respect to the lead to generate different physiological effects (e.g., therapeutic effects), permitting stimulation to be oriented directionally. In some examples, leads 16 may be, at least in part, paddle-shaped (e.g., a "paddle" lead), and may include an array of electrodes arranged as contacts or pads on a common surface, which may or may not be substantially flat and planar.

In some examples, leads 16 may not be attached to respective hypoglossal nerves 26, and may be implanted via needle or introducer such that electrodes 22A-22D and electrodes 24A-24D are proximate to respective hypoglossal nerves 26. Also, because leads 16 may not attach to respective hypoglossal nerves 26, the isodiametric distal end can also be removed relatively easily. For example, leads 16 may be isodiametric leads that are implanted percutaneously, and therefore, may not wrap around hypoglossal nerves 26. Because leads 16 may not wrap around hypoglossal nerves 26, if removal of leads 16 is desired, it may be possible to remove leads 16 from tissue without impacting hypoglossal nerves 26 (e.g., unlike leads with cuff electrodes that wrap around hypoglossal nerves 26). In some examples, leads 16 include tines that deploy after insertion to fixate leads 16 within tongue 20 (e.g., base of tongue 20 where protrusor muscles are located, as one non-limiting example).

Isodiametric may refer to there not being any portions of leads 16 that are larger diameter in the distal sections that will impede the lead being pulled out through the lead tract (which might be encapsulated) through the tissue. Leads 16 may have tines which are not isodiametric, but if the tines are the only portion that are isodiametric it will be easier to remove.

In the above examples, leads 16 are not affixed to respective hypoglossal nerves 26. However, in some examples, leads 16 may be affixed to respective hypoglossal nerves 26. For instance, one or more of electrodes 22A-22D and electrodes 24A-24D may be cuff electrodes that attach to respective hypoglossal nerves 26.

The implant location of leads 16 and the location of electrodes 22A-22D and electrodes 24A-24D is provided as illustration only, and should not be considered limiting. Also, an example in which each one of leads 16 includes four electrodes is also provided for example purposes. There may be more or fewer electrodes than four electrodes in different examples of leads 16.

In some examples, some of electrodes 22A-22D and electrodes 24A-24D may be configured for stimulation and others may be configured to sensing. In some examples, each of electrodes 22A-22D and electrodes 24A-24D may be selectively configured to provide stimulation or sensing.

Referring back to FIG. 1, as described above, IMDs 14 may be configured to deliver electrical stimulation to treat OSA. For example, electrical stimulation therapy generated by IMDs 14 and delivered via one or more electrodes 22 and 24 may activate protrusor muscles to move tongue 20 forward, for instance, to promote a reduction in obstruction or narrowing of the upper airway during sleep. As used herein, the term "activated" with regard to the electrical stimulation of the protrusor muscles refers to electrical stimulation that causes depolarization or an action potential of the cells of the nerve (e.g., hypoglossal nerves 26) or stimulation at the neuro-muscular junction between the hypoglossal nerves 26 and the protrusor muscles (e.g., at the motor points) innervating the protrusor muscles and motor points and subsequent depolarization and mechanical contraction of the protrusor muscle cells of the protrusor muscles. In some examples, the protrusor muscles may be activated directly by the electrical stimulation therapy.

The protrusor muscles, on a first side of tongue 20 (e.g., the left or right side of tongue 20), may be activated by a medial branch of a first hypoglossal nerve (e.g., hypoglossal nerve 26A or 26B), and the protrusor muscles, on a second side of tongue 20 (e.g., the other of the left or right side of tongue 20), may be activated by a medial branch of a second hypoglossal nerve (e.g., the other of hypoglossal nerve 26A or 26B). The medial branch of hypoglossal nerve 26A or 26B may also be referred to as the XIIth cranial nerve. The hyoglossus and styloglossus muscles (not shown in FIG. 1 or 2), which cause retraction and elevation of tongue 20, are activated by a lateral branch of the hypoglossal nerves 26.

One or more electrodes 22 and 24 may be used to deliver bilateral or unilateral stimulation to the protrusor muscles via the medial branch of the hypoglossal nerves 26 or branches of the hypoglossal nerves 26 (e.g. such as at the motor point where a terminal branch of the hypoglossal nerves 26 interfaces with respective muscle fibers of the protrusor muscles). For example, one or more electrodes 22 and 24 may be coupled to output circuitry of IMDs 14, respectively, to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMDs 14 may deliver electrical stimulation to selectively activate the protrusor muscles or portions of the protrusor muscles during unilateral stimulation of the left or right protrusor muscles.

As illustrated, lead 16A may be implanted such that one or more of electrodes 22 deliver electrical stimulation to stimulate hypoglossal nerve 26A or motor points of protrusor muscles on a first side of tongue 20, and therefore cause the protrusor muscles on the first side to activate. In such examples, the electrical stimulation from one or more electrodes 22 may not be of sufficient amplitude to stimulate hypoglossal nerve 26B or motor points of protrusor muscles on the second side of tongue 20 and cause the protrusor muscles on the side to activate.

In one or more examples, IMDs 14 may alternate stimulation (e.g., provide bilateral stimulation), rather than continuous stimulation to both hypoglossal nerves 26 to reduce fatigue. For instance, continuous stimulation may cause protrusor muscles to be continuously in a protruded state. This continuous contraction may cause the protrusor muscles to fatigue. In such cases, due to fatigue, the stimulation may not cause the protrusor muscles to maintain a protruded state (or a higher intensity of the electrical stimulation may be needed to cause the protrusor muscles to remain in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain the advancing of tongue 20, while permitting the protrusor muscles that were previously activated to rest. Hence, by cycling between alternate stimulation of the left and right protrusor muscles, tongue 20 can remain in the protruded state, while one of the first or second set of protrusor muscles is at rest.

There may be various ways in which leads 16 are implanted in patient 14. As one example, a surgeon may insert a needle (also called introducer needle) through the lower part of the jaw and in tongue 20 starting from the back of tongue 20. The surgeon may insert the needle until a distal tip of the needle reaches a point at or adjacent to the tip of tongue 20, angling the needle to be extended proximate to the hypoglossal nerves 26 and to the motor points. In some examples, the needle may include one or more electrodes (e.g., one to four electrodes) at the distal end, and the surgeon may cause the one or more electrodes of the needle to output electrical stimulation (e.g., in the form of controlled current pulses or controlled voltage pulses), which in turn causes a physiological response such as activation of the protrusor muscles and protrusion of tongue 20. The surgeon may adjust the location of the needle based on the physiological response to determine a location in tongue 20 that provides effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 20. Then, the surgeon may remove the needle, leaving behind the guidewire.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes that the surgeon can use to test stimulation of tongue 20 to ensure that electrodes 22A-22D and electrodes 24A-24D will be located in the correct location, relative to the target nerve tissue (e.g., motor points). Once the introducer is in place, the surgeon may remove the guidewire. In some examples, the introducer may be flexible or curved to ease placement of the introducer in patient 12.

The surgeon may prepare leads 16 for insertion. In some examples, there may be an additional sheath placed over leads 16 that holds fixation member(s) (e.g., tines) in place. Use of such an additional sheath is not necessary in all examples. Because leads 16 may be highly flexible, in some examples, the surgeon may place a stylet through leads 16 to provide some rigidity and allow leads 16 to traverse through tongue 20 under a pushing force. Use of a stylet may not be necessary in all examples.

The surgeon may put leads 16 through the introducer such that one or more electrodes 22 and 24 are proximate to the hypoglossal nerves 26 (e.g., such that distal ends of leads 16 are near tip of tongue 20 as one non-limiting example). Electrodes 22 and 24 may be proximate to hypoglossal nerves 26 and/or motor points of the protrusor muscles due to the needle creating an opening near hypoglossal nerves 26 and/or motor points of the protrusor muscle. The surgeon may then tunnel the proximal end of leads 16 back to a connection with respective IMDs 14.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the needle, and/or the introducer.

As described above, IMDs 14 may be configured to deliver bilateral stimulation (e.g., IMD 14A may deliver electrical stimulation, then IMD 14B, then IMD 14A, and so forth) to avoid fatigue. For bilateral stimulation, IMDs 14 may synchronize or otherwise coordinate timing of when IMDs 14 are to stimulate. However, there may be various different ways in which to deliver bilateral stimulation.

As one example, IMD 14A may deliver electrical stimulation to hypoglossal nerve 26A, and IMD 14B may start to deliver electrical stimulation to hypoglossal nerve 26B only until after IMD 14A completes delivering electrical stimulation to hypoglossal nerve 26A. As another example, IMD 14A may deliver electrical stimulation to hypoglossal nerve 26A, and IMD 14B may start to deliver electrical stimulation to hypoglossal nerve 26B before IMD 14A completes delivery of electrical stimulation to hypoglossal nerve 26A (e.g., there is partial overlap in the stimulation provided by IMDs 14).

As another example, IMD 14A may ramp up the amplitude of the electrical stimulation that is delivered to hypoglossal nerve 26A until the amplitude reaches a plateau for some time. IMD 14A may then ramp down the amplitude of the electrical stimulation that is delivered to hypoglossal nerve 26A. As IMD 14A is ramping down the amplitude of the electrical stimulation that is delivered to hypoglossal nerve 26A, IMD 14B may begin to ramp up the amplitude of the electrical stimulation that is delivered to hypoglossal nerve 26B until the amplitude reaches a plateau for some time. IMD 14B may then ramp down the amplitude of the electrical stimulation that is delivered to hypoglossal nerve 26B. As IMD 14B is ramping down the amplitude of the electrical stimulation that is delivered to hypoglossal nerve 26B, IMD 14A may begin to ramp up the amplitude of the electrical stimulation that is delivered to hypoglossal nerve 26B until the amplitude reaches a plateau for some time, and so forth.

In some examples, to ensure coordinated operation (e.g., synchronization but not limited to synchronization), IMDs 14 may communicate with one another. For instance, IMD 14A may communicate to IMD 14B the time and duration of the electrical stimulation that IMD 14A is to deliver so that IMD 14B can determine when to start the electrical stimulation that IMD 14B is to deliver. As another example, IMD 14A may instruct IMD 14B when IMD 14B is to deliver electrical stimulation, and IMD 14B may in turn deliver electrical stimulation at the time instructed by IMD 14A.

Synchronization of electrical stimulation is one example when IMDs 14 may communicate to one another. However, there may be other examples where IMDs 14 may communicate to one another, including examples where bilateral stimulation is not necessarily needed.

As one example, IMDs 14 may be configured to determine therapy parameters for the electrical stimulation signals, and communicate such therapy parameters to each other. For instance, IMD 14A may communicate amplitude, pulse width, and/or frequency of the electrical stimulation signal that IMD 14A is to deliver or instruct IMD 14B of the amplitude, pulse width, and/or frequency of the electrical stimulation signal that IMD 14B is to deliver.

In some examples, one or both of IMDs 14 may include additional sensors such as sensors to sense motion or respiration rate (e.g., based on accelerometers within one or more both of IMDs 14). Respiration rate may be sensed based on impedance, alternatively or in addition to using sensors. In some examples, one or both of IMDs 14 may include a microphone configured to sense trachea sounds associated with breathing or snoring of patient 12. In such examples, IMDs 14 may be configured to communicate information indicative of sensed motion or respiration rate and/or information indicative of sensed trachea sounds.

For instance, IMD 14A may determine based on the motion or respiration rate that patient 12 is in a deep sleep, and is therefore more likely to experience OSA. In response, IMD 14A may increase the amplitude of the electrical stimulation signal that IMD 14A is to deliver. IMD 14A may communicate the information indicative of the motion or respiration rate to IMD 14B so that IMD 14B can similarly determine that patient 12 is in a deep sleep, and increase the amplitude of the electrical stimulation signal that IMD 14B is to deliver. IMDs 14 may similarly use trachea sounds to control therapy parameters for the electrical stimulation signals.

As another example, IMDs 14 may communicate with one another to confirm a patient characteristic. For instance, IMD 14A may determine from the microphone of IMD 14A configured to sense trachea sounds that patient 12 is snoring. However, prior to changing any therapy parameter, IMD 14A may first transmit information indicative of the trachea sound to IMD 14B. IMD 14B may determine whether the microphone of IMD 14B configured to sense trachea sounds also received sounds indicating that patient 12 is snoring. If IMD 14B confirms that patient 12 is snoring, IMD 14B may communicate to IMD 14A confirming that patient 12 is snoring, and both IMDs 14 may increase the amplitude and/or adjust another parameter like pulse width or duty cycle of respective electrical stimulation signals. IMDs 14 may similarly use motion or respiration rate to confirm patient characteristic before changing therapy parameters.

The example sensors such as motion sensors and microphones need not necessarily be part of IMDs 14, and may be coupled to IMDs 14. For instance, the sensors may be located elsewhere in patient 12 and output information (e.g., via wired or wireless techniques) to respective IMDs 14.

In some examples, IMDs 14 may communicate with one another to change programs stored in respective IMDs 14. For instance, FIG. 1 illustrates programmer 18. Programmer 18 may generally be described as a hand-held computing device. The programmer may be, for example, a notebook computer, a cell phone, or a workstation, for example. Programmer 18 may communicate therapy parameters to program IMDs 14.

Programmer 18 may be configured to communicate using RF telemetry, inductive telemetry, etc. In one or more examples, rather than programmer 18 communicating with both IMDs 14, programmer 18 may communicate with one of IMDs 14 (e.g., IMD 14A in FIG. 1). IMD 14A may then forward changes to programs to IMD 14B.

This disclosure describes example ways in which IMDs 14 may communicate with one another. In accordance with one or more examples described in this disclosure, IMDs 14 may encode information that is to be communicated in the electrical stimulation signals that IMDs 14 output. For instance, IMD 14A may modulate (e.g., phase, pulse-width, frequency, and/or amplitude) the electrical stimulation signal that IMD 14A is to output with information that IMD 14A is to communicate to IMD 14B. Electrodes 22 configured to output the electrical stimulation signal may output the electrical stimulation signal to stimulate hypoglossal nerve 26A. In addition, electrodes 24 configured to sense electrical signals may sense the electrical stimulation signal from IMD 14A. IMD 14B may then demodulate the sensed electrical stimulation signal to retrieve the information that IMD 14A communicated to IMD 14B.

For instance, the electrical stimulation signal that IMD 14A outputs may be considered as a carrier signal. Communication circuitry within IMD 14A may modulate (e.g., phase, pulse-width, frequency, or amplitude) the carrier signal to encode the information that is to be communicated on the carrier signal. IMD 14B may receive the modulated carrier signal. Communication circuitry within IMD 14B may demodulate the carrier signal to retrieve the information.

In some examples, the electrical stimulation signal that IMD 14A outputs may be sufficient to stimulate hypoglossal nerve 26A to cause tongue 20 to advance (e.g., protrude). The tissue of tongue 20 may be electrically lossy such that the electrical stimulation signal that IMD 14A outputs may not be sufficient to stimulate hypoglossal nerve 26B sufficiently to cause tongue 20 to advance. However, there may be sufficient intensity in the electrical stimulation signal that IMD 14B can retrieve the information embedded in the electrical stimulation signal that IMD 14A outputed.

Communicating information with electrical stimulation signals may be beneficial for various reasons. As one example, not all IMDs 14 necessarily need to include complex communication circuitry that tends to consume power. For instance, programmer 18 may be configured to use Bluetooth or other such communication protocols to transmit and receive information. Rather than each of IMDs 14 including communication circuitry configured to communicate using Bluetooth or other such communication protocols, IMD 14A may include such communication circuitry, and IMD 14B may not include such communication circuitry. IMD 14A may then transmit information to IMD 14B via the electrical stimulation signals.

As another example, OSA treatment may be such that embedding information on the electrical stimulation signals minimally impacts the therapy efficacy. For example, there may be wide range of amplitudes and pulse widths that can cause tongue 20 to advance. Amplitude modulation causes the amplitude of the electrical stimulation signal to change. The amount that the amplitude of the electrical stimulation signal can be modulated without impacting therapy efficacy may be relative large, providing for robust communication (e.g., the signal-to-noise ratio of the embedded signal can be relatively high). Phase modulation causes the phase of the electrical stimulation signal to change. The amount that the phase of the electrical stimulation signal can be modulated without impacting therapy efficacy may be relative large, providing for robust communication (e.g., the signal-to-noise ratio of the embedded signal can be relatively high). In some examples, amplitude and phase modulation may be combined.

Accordingly, this disclosure describes examples of a system for OSA therapy. IMD 14A may be implantable within a head of patient 12 and coupled to a first set of electrodes 22 (e.g., of lead 16A) implantable proximate to hypoglossal nerve 26A within tongue 20 of patient 12. IMD 14B may be implantable within the head of patient 12 and coupled to a second set of electrodes 24 (e.g., of lead 16B) implantable proximate to hypoglossal nerve 26B within tongue 20 of patient 12. As an example, IMD 14A is implantable in the head of patient 12 behind a first ear, and IMD 14B is implantable in the head of patient 12 behind a second ear.

In one or more examples, IMD 14A is configured to deliver an electrical stimulation signal to hypoglossal nerve 26A that causes tongue 20 of patient 12 to advance and includes information to communicate to IMD 14B. IMD 14B is configured to receive the information included in the electrical stimulation signal delivered by IMD 14A via sensing of the electrical stimulation signal by one or more electrodes of the second set of electrodes 24.

Similarly, IMD 14B is configured to deliver an electrical stimulation signal to hypoglossal nerve 26B that causes tongue 20 of patient 12 to advance and includes information to communicate to IMD 14A. IMD 14A is configured to receive the information included in the electrical stimulation signal delivered by IMD 14B via sensing of the electrical stimulation signal by one or more electrodes of the first set of electrodes 22.

As described above, electrodes 22 and 24 may be formed as exposed coil or cable of respective leads 16 to provide flexibility. However, electrodes 22 and 24 may be formed in other ways as well including ring electrodes, segmented electrodes, paddle electrodes, cuff electrodes, and the like.

There may be various examples of the information that IMDs 14 communicate to one another. The information to communicate includes one or more of information for when to stimulate (e.g., for coordinated operation), information of an amplitude, pulse width, or frequency of an electrical stimulation signal that IMDs 14 are to output, information indicative of patient characteristics, and information indicative of changes to programs.

There may be various examples of patient characteristics. For instance, IMDs 14 may include or be communicatively coupled to one or more sensors to sense motion or respiration rate. As another example, IMDs 14 may include or be communicatively coupled to a microphone configured to sense trachea sounds associated with breathing or snoring of the patient. The patient characteristics may include motion or respiration rate and/or whether patient 12 is snoring. For instance, the information that IMDs 14 communicate to one another may include information indicative of sensed motion or respiration rate, or may include information indicative of the sensed trachea sounds.

Figure 3:
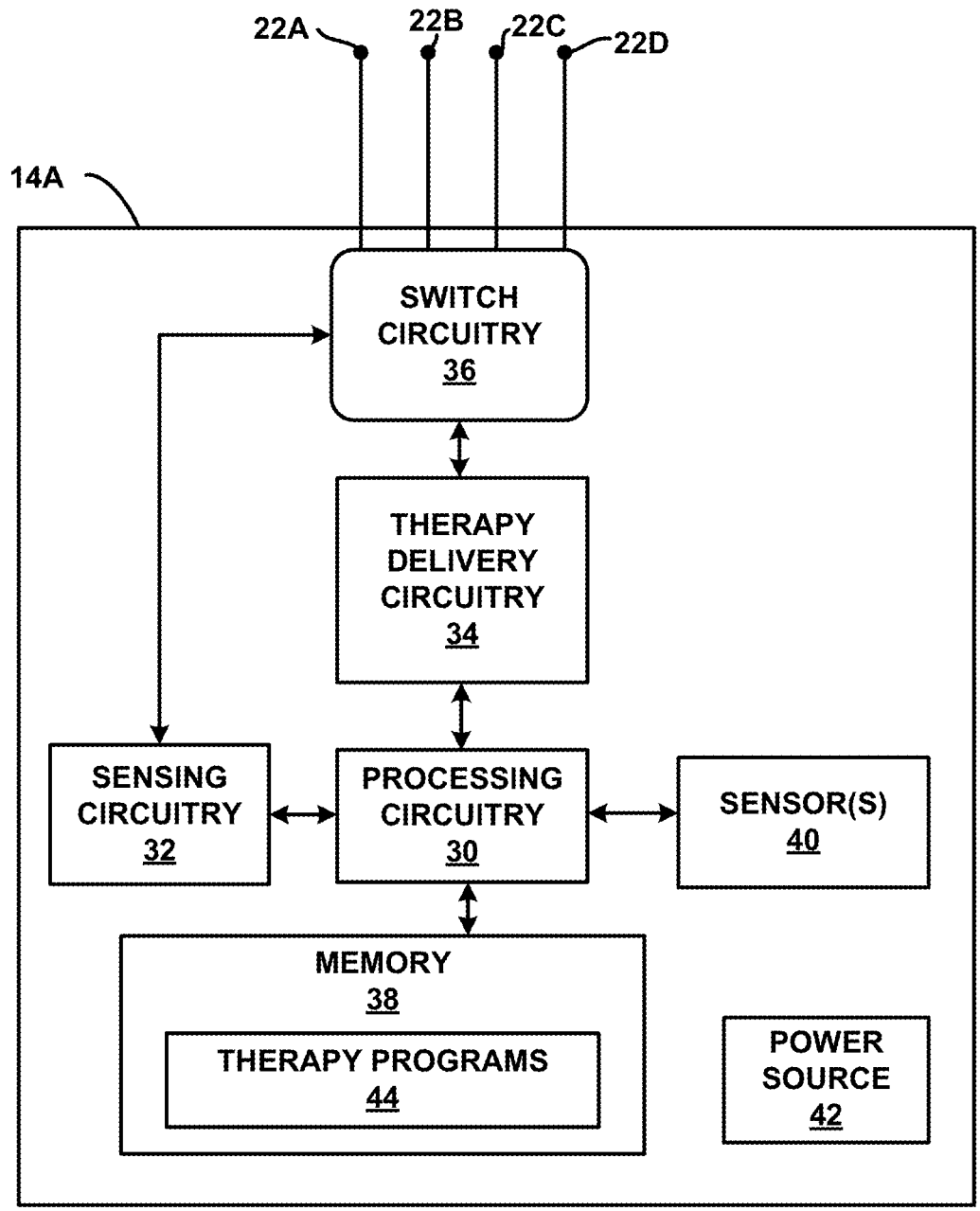
FIG. 3 is a block diagram illustrating an example of an IMD.

FIG. 3 is a block diagram illustrating example configurations of implantable medical devices (IMDs) which may be utilized in the system of FIG. 1. For instance, FIG. 3 illustrates an example of IMD 14A. IMD 14B may be similar or identical to IMD 14A.

As shown in FIG. 3, IMD 14A includes processing circuitry 30, sensing circuitry 32, therapy delivery circuitry 34, switch circuitry 36, memory 38, one or more sensors 40, and power source 42. IMD 14A may include a greater or fewer number of components. For example, IMD 14A may include telemetry circuitry such as telemetry circuitry to communicate with programmer 16. However, it may not be necessary for all IMDs 14 to include such telemetry circuitry. For instance, IMD 14A may form a bridge between IMD 14B and programmer 16, and may transmit information from programmer 16 for IMD 14B, receive information for programmer 16 from IMD 14B, and transmit information to programmer 16 from IMD 14B using the techniques described in this disclosure.

Switch circuitry 36 may be configured to, in response to instructions from processing circuitry 30, switch the coupling of electrodes 22 between sensing circuitry 32 and therapy delivery circuitry 34. In this way, electrodes 22 may function as stimulation electrodes or sensing electrodes. In some examples, after initial setting, some of electrodes 22 may be set as stimulation electrodes, and other electrodes 22 may be set as sensing electrodes. In such examples, switch circuitry 36 may form a passthrough device that passes sensed electrical signals to sensing circuitry 32 and passes stimulation electrical signals generated by therapy delivery circuitry 34.

In some examples, therapy delivery circuitry 34 may include a plurality of regulated current sources or sinks, with each current source or sink coupled to one of electrodes 22. In such examples, therapy delivery circuitry 34 may control each current source or sink and switching between electrodes 22 for delivery of stimulation signals may not be necessary for therapy delivery since each one of electrodes 22 is individually controllable.

One or more sensors 40 may be configured to sense posture or position of patient 12. For example, one or more sensors 40 may include an accelerometer to determine if patient 12 is lying down. Another example of the one or more sensors 40 is a motion sensor, and movement sensed by the motion sensor may indicate if patient 12 is having restless sleep, which may be indicative of the onset of OSA. Additional examples of the sensors 40 include acoustical sensors or a microphone for detecting vibrations in the upper airway or trachea. Vibrations in the upper airway or trachea may be indicative of the onset of OSA. In some examples, processing circuitry 30 may control delivery of therapy based on information received from the one or more sensors 40, such as delivery of therapy after sensing an onset of OSA.

Although one or more sensors 40 are illustrated as part of IMD 14A, the example techniques are not so limited. In some examples, one or more sensors 40 may be external to IMD 14A and communicatively coupled (e.g., wired or wirelessly) with IMD 14A.

Also, processing circuitry 30 may transmit such sensed information to IMD 14B. For example, one or more sensors 40 may sense motion or respiration rate, and the information that IMD 14A communicates to IMD 14B may include information indicative of motion or respiration rate. As another example, one or more sensors 40 may include a microphone configured to sense trachea sounds associated with breathing or snoring of patient 12, and the information that IMD 14A communicates to IMD 14B includes information indicative of the trachea sounds.

In some examples, electrodes 22 may be configured to sense an electrical stimulation signal that IMD 14B outputted. The electrical stimulation signal that IMD 14B outputted may include information that IMD 14B communicates to IMD 14A.

In general, IMD 14A may comprise any suitable arrangement of hardware, alone or in combination with software and/or firmware, to perform the techniques attributed to IMD 14A and processing circuitry 30, therapy delivery circuitry 34, and sensing circuitry 32. In various examples, processing circuitry 30 may be one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 14A may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

Processing circuitry 30 and/or other components of IMD 14A may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 38 may store the instructions (e.g., object code) of the software that processing circuitry 30 receives and executes, or another memory within IMD 14A (not shown) may store such instructions.

IMD 14A also, in various examples, may include a memory 38, such as random access memory (RAM), read only memory (ROM), programmable read only memory (PROM), erasable programmable read only memory (EPROM), electronically erasable programmable read only memory (EEPROM), or flash memory, comprising executable instructions for causing processing circuitry to perform the actions attributed to them. Moreover, although sensing circuitry 32, processing circuitry 30, therapy delivery circuitry 34, and switch circuitry 36 are described as separate circuitry, in some examples, sensing circuitry 32, processing circuitry 30, therapy delivery circuitry 34, and switch circuitry 36 are functionally integrated. In some examples, sensing circuitry 32, processing circuitry 30, therapy delivery circuitry 34, and switch circuitry 36 correspond to individual hardware units, such as ASICs, DSPs, FPGAs, or other hardware units.

Memory 38 stores therapy programs 44 (also called stimulation programs) that specify stimulation parameter values for the electrical stimulation provided by IMD 14A. Memory 38 may also store instructions for execution by processing circuitry 30, in addition to therapy programs 44. Information related to sensed parameters of patient 12 (e.g., from sensing circuitry 32 or the one or more sensors 40 of IMD 14A) may be recorded for long-term storage and retrieval by a user, and/or used by processing circuitry 30 for adjustment of stimulation parameters (e.g., amplitude, pulse width, and pulse rate). In some examples, memory 38 includes separate memories for storing instructions, electrical signal information, and therapy programs 44. In some examples, processing circuitry 30 may select new stimulation parameters for a stimulation program 44 or new stimulation program from therapy programs 44 to use in the delivery of the electrical stimulation based on patient input and/or monitored physiological states after termination of the electrical stimulation.

Generally, therapy delivery circuitry 34 generates and delivers electrical stimulation under the control of processing circuitry 30. In some examples, processing circuitry 30 controls therapy delivery circuitry 34 by accessing memory 38 to selectively access and load at least one of therapy programs 44 to therapy delivery circuitry 34. For example, in operation, processing circuitry 30 may access memory 38 to load one of therapy programs 44 to therapy delivery circuitry 34.

By way of example, processing circuitry 30 may access memory 38 to load one of therapy programs 44 to control therapy delivery circuitry 34 for delivering the electrical stimulation to patient 12. A clinician or patient 12 may select a particular one of therapy programs 44 from a list using a programming device, such as a patient programmer or a clinician programmer. Processing circuitry 30 may receive the selection via telemetry circuitry. Therapy delivery circuitry 34 delivers the electrical stimulation to patient 12 according to the selected program for an extended period of time, such as minutes or hours while patient 12 is asleep (e.g., as determined from the one or more sensors 40). For example, processing circuitry 30 may control switch circuitry 36 to couple electrodes 22 to therapy delivery circuitry 34.

Therapy delivery circuitry 34 delivers electrical stimulation according to stimulation parameters. In some examples, therapy delivery circuitry 34 delivers electrical stimulation in the form of electrical pulses. In such examples, relevant stimulation parameters may include a voltage or current pulse amplitude, a pulse rate, a pulse width, a duty cycle, and/or the combination of electrodes 22 that therapy delivery circuitry 34 uses to deliver the stimulation signal. In some examples, therapy delivery circuitry 34 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 22 therapy delivery circuitry 34 uses to deliver the stimulation signal.

In some examples, the stimulation parameters for the therapy programs 44 may be selected to cause the protrusor muscles to a protruded state (e.g., to open-up the airway). An example range of stimulation parameters for the electrical stimulation that are likely to be effective in treating OSA (e.g., upon application to the hypoglossal nerves 26 to cause the protrusor muscles to advance or upon application to motor points such as motor points of hypoglossal nerves 26), are as follows:

a. Frequency or pulse rate: between about 30 Hz and about 50 Hz. In some examples, the minimum target frequency is used which can achieve muscle tetany (e.g., constant contraction) and provide the required force to open the airway.

b. Current Amplitude: between about 0.5 milliamps (mA) and about 10 mA, and more generally from 0.5 mA to 3 mA, and approximately 1.5 mA.

c. Pulse Width: between about 100 microseconds (μs) and about 500 μs. In some examples, a pulse width of 150 μs might be used for reduced power consumption. In some particular examples, the pulse width is approximately 210 μs. In some cases, shorter pulse widths may be used in conjunction with higher current or voltage amplitudes.

As described above, therapy delivery circuitry 34 may deliver electrical stimulation to hypoglossal nerve 26A, and then alternate deliver of electrical stimulation with IMD 14B. In some examples, to synchronize communication, IMD 14A may communicate information to IMD 14B, and in accordance with one or more examples described in this disclosure, IMD 14A may include information that IMD 14A is to communicate to IMD 14B in the electrical stimulation signal the IMD 14A delivers. For instance, IMD 14A (e.g., with processing circuitry 30 or therapy delivery circuitry 34) may modulate an electrical stimulation signal that IMD 14A outputs on electrodes 22 as a way to communicate information to IMD 14B. Similarly, IMD 14A may receive information from IMD 14B. For instance, IMD 14A (e.g., with processing circuitry 30 or sensing circuitry 32) may demodulate an electrical stimulation signal from IMD 14B to retrieve information that IMD 14B communicates to IMD 14A.

There may be various types of information that IMD 14A communicates to IMD 14B. For instance, IMD 14A the information may include one or more of information for when to stimulate (e.g., when IMD 14B is to stimulate and for how long), information of an amplitude, pulse width, and/or frequency of an electrical stimulation signal that IMD 14B is to output, information indicative of patient characteristics (e.g., whether patient 12 is snoring or not so that IMD 14B can determine whether to stimulate in response to sensed snoring or confirm that IMD 14A is to stimulate), and information indicative of changes to programs.

For instance, like IMD 14A, IMD 14B may store therapy programs like therapy programs 44. If there are any changes to therapy programs, IMD 14A may include such information in the electrical stimulation signal that IMD 14A outputs. As another example, processing circuitry 30 may be configured with firmware, and when newer versions of the firmware are released, IMD 14A may transmit the information of the newer versions of the firmware to IMD 14B.

In some examples, IMD 14A may transmit or receive error codes to or from IMD 14B. For instance, the information that IMD 14A transmits to or receives from IMD 14B may include information about whether there are any system errors in IMD 14A or IMD 14B. As an example, if IMD 14A determines that therapy delivery circuitry 34 is not operating correctly, IMD 14A may transmit such information to IMD 14B, and IMD 14B may determine to transmit continuous stimulation to treat OSA. For instance, because therapy delivery circuitry 34 cannot deliver therapy, IMD 14B may be tasked with providing therapy that keeps the tongue protruded (e.g., advanced). To ensure that the tongue remains protruded (e.g., advanced), IMD 14B may provide continuous stimulation since IMD 14A cannot provide stimulation. That is, bilateral stimulation may not be available since IMD 14A cannot provide stimulation; therefore, IMD 14B may provide continuous stimulation.

Power source 42 delivers operating power to the components of IMD 14A. Power source 42 may include a battery and a power generation circuit to produce the operating power. In some examples, the battery may be rechargeable to allow extended operation. Recharging may be accomplished through proximal inductive interaction between an external charger and an inductive charging coil within IMD 14A. In other examples, an external inductive power supply may transcutaneously power IMD 14A whenever electrical stimulation is to occur.

Figure 4:
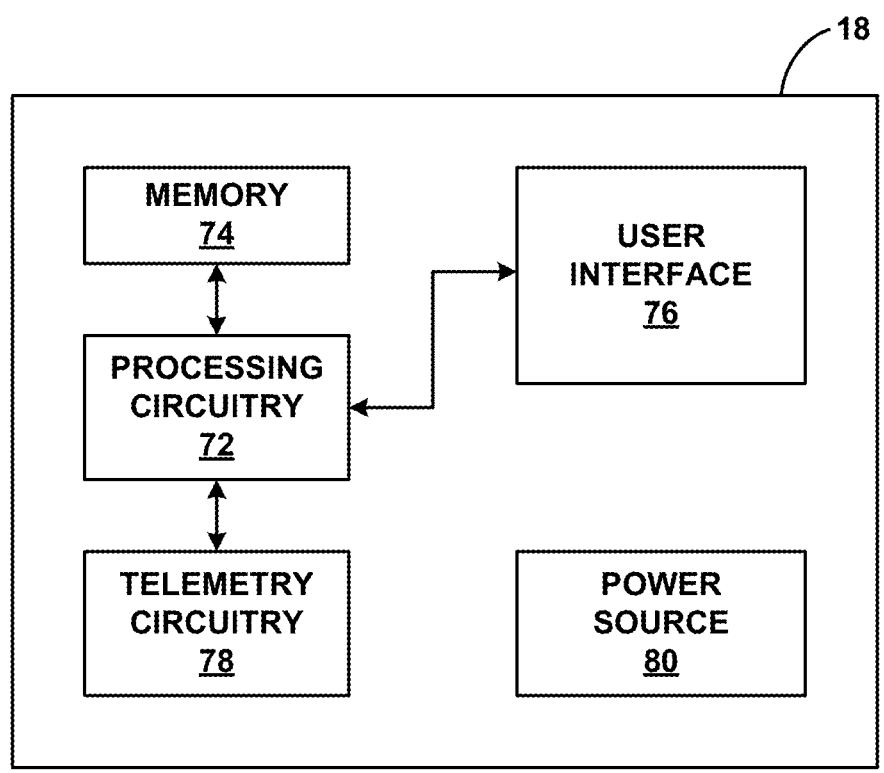
FIG. 4 is a block diagram illustrating an example of a programmer.

FIG. 4 is a block diagram illustrating an example configuration of an external programmer 18. While programmer 18 may generally be described as a hand-held computing device, the programmer 18 may be a notebook computer, a cell phone, or a workstation, for example. As illustrated in FIG. 4, external programmer 18 may include processing circuitry 72, memory 74, user interface 76, telemetry circuitry 78, and power source 80.

In general, programmer 18 comprises any suitable arrangement of hardware, alone or in combination with software and/or firmware, to perform the techniques attributed to programmer 18, and processing circuitry 72, user interface 76, and telemetry module 78 of programmer 18. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 38 of IMD 14A. The stimulation programs stored in memory 74 may be downloaded into memory 38 of IMD 14A and similar memory of IMD 14B.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 12 or a caregiver via user interface 76. Although not shown, programmer 18 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 14A and programmer 18 under the control of processing circuitry 72. Telemetry circuitry 78 may also be configured to communicate with another computing device via wireless communication techniques, or direct communication through a wired connection. In some examples, telemetry circuitry 78 may be substantially similar to the telemetry circuitry of IMD 14A described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 18 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 18 without needing to establish a secure wireless connection.

Power source 80 delivers operating power to the components of programmer 18. Power source 80 may include a battery and a power generation circuit to produce the operating power. In some examples, the battery may be rechargeable to allow extended operation.

Figure 5A:
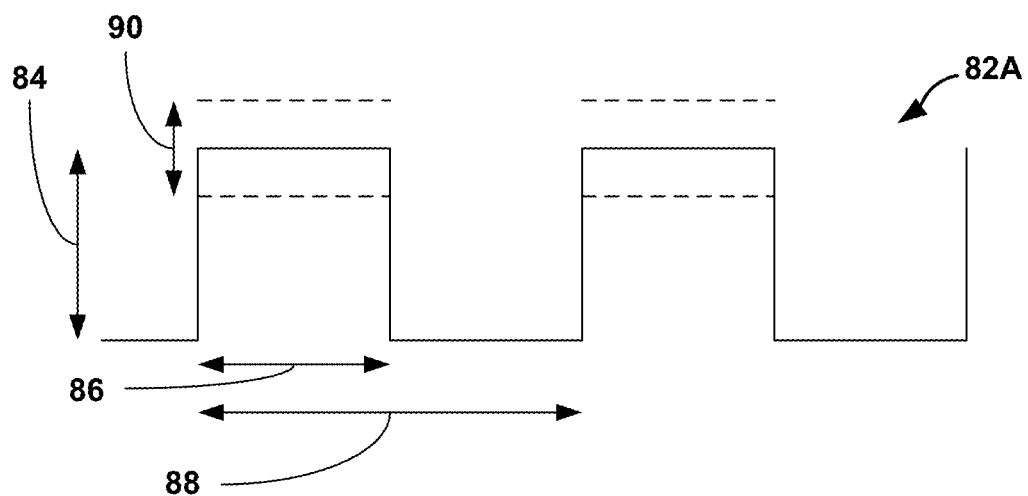
FIGS. 5A and 5B are conceptual diagrams illustrating examples of stimulation signals that include information that a first medical device communicates to a second medical device.
Figure 5B:
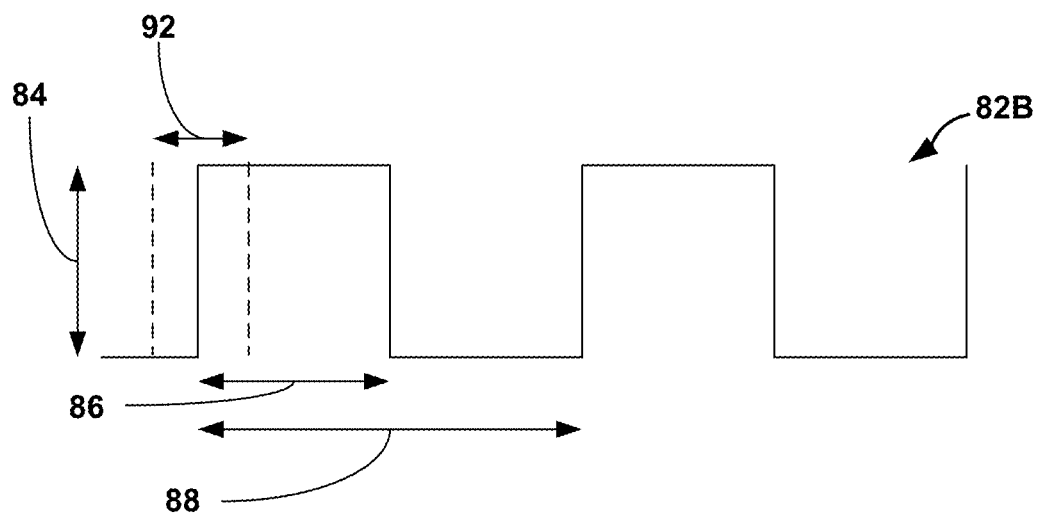

FIGS. 5A and 5B are conceptual diagrams illustrating examples of stimulation signals that include information that a first medical device communicates to a second medical device. For instance, FIG. 5A illustrates an example of IMD 14A amplitude modulating electrical stimulation signal 82A to include information that IMD 14A communicates to IMD 14B. FIG. 5B illustrates an example of IMD 14A pulse width modulating electrical stimulation signal 82B to include information that IMD 14A communicates to IMD 14B.

In the example of FIGS. 5A and 5B, electrical stimulation signals 82A and 82B may be carrier signals. The amplitude 84 of electrical stimulation signals 82A and 82B may be approximately 2 mA, the pulse width 86 of electrical stimulation signals 82A and 82B may be approximately 300 μs, and the period 88 of electrical stimulation signals 82A and 82B may be approximately 25 ms (e.g., frequency of 40 Hz).

For the amplitude modulation, the amplitude of electrical stimulation signal 82A may be modulated by amplitude 90 (e.g., the amplitude 84 may be increased or decreased) to embed information that IMD 14A communicates to IMD 14B. An example range of amplitude 90 may be 0 to 20 mA or 0 to 20 mV (if voltage controlled). For pulse width modulation, the pulse width of electrical stimulation signal 82B may be modulated by amplitude 92 (e.g., the pulse width 86 may be increased or decreased) to embed information that IMD 14A communicates to IMD 14B. An example range of amplitude 92 may be 50 to 1000 microseconds.

FIGS. 5A and 5B illustrate two examples of modulation schemes that IMDs 14A and 14B may utilized. However, the example techniques are not so limited. IMDs 14A and 14B may utilize various other modulation schemes such as quadrature amplitude modulation (QAM), phase-shift keying (PSK), and the like.

Figure 6:
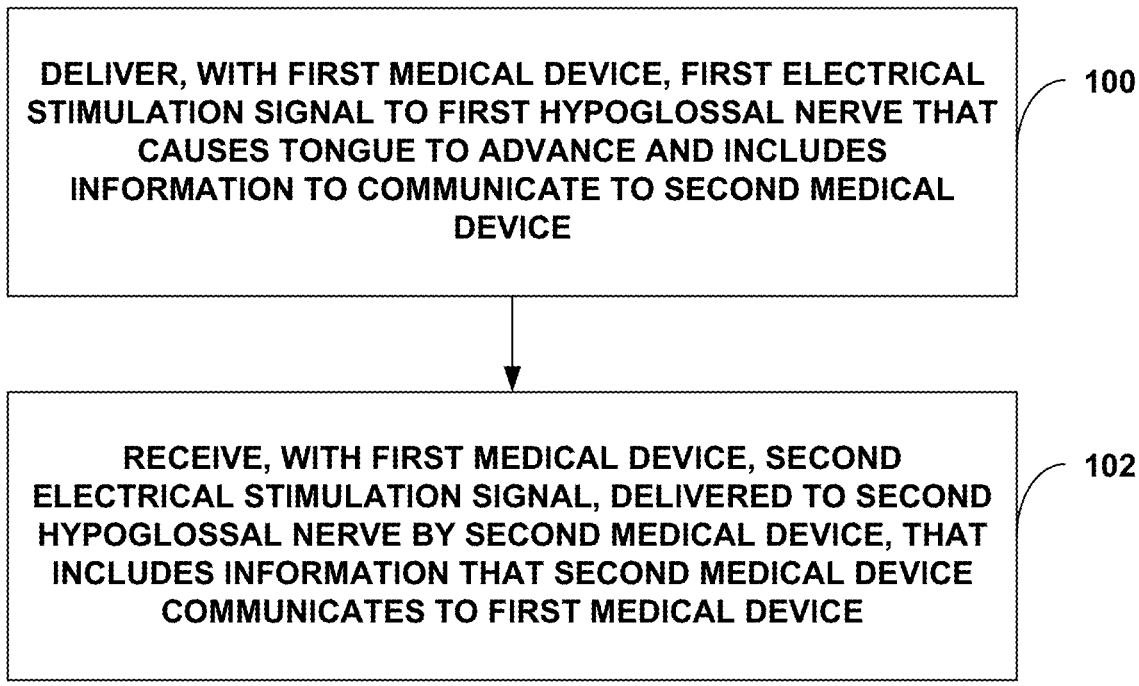
FIG. 6 is a flowchart illustrating example techniques of operation.

FIG. 6 is a flowchart illustrating example techniques of operation. In the example of FIG. 6, IMD 14A (e.g., a first medical device), that is implantable within a head or neck of patient 12 and coupled to first set of electrodes 22 (e.g., of lead 16) implantable proximate to first hypoglossal nerve 26A within tongue 20 of patient 12, may deliver a first electrical stimulation signal to the first hypoglossal nerve 26A that causes the tongue 20 of the patient 12 to advance and includes information to communicate to IMD 14B (e.g., a second medical device) implantable within the head or neck of the patient 12 and coupled to second set of electrodes 24 implantable proximate to second hypoglossal nerve 26B within the tongue 20 of the patient 12 (100). As one example, IMD 14A may modulate the first electrical stimulation signal to include the information to communicate to the second medical device.

IMD 14A may receive a second electrical stimulation signal, delivered to the second hypoglossal nerve 26B by the second medical device (e.g., IMD 14B), that includes information that IMD 14B communicates to IMD 14A (102). For example, IMD 14A may demodulate the second electrical stimulation signal to retrieve the information that the second medical device (e.g., IMD 14B) communicates to the first medical device (e.g., IMD 14A).

As one example, the information to communicate to the second medical device (e.g., IMD 14B) includes one or more of information for when to stimulate, information of an amplitude, pulse width, or frequency of an electrical stimulation signal that the second medical device is to output, information indicative of patient characteristics, and information indicative of changes to programs. In some examples, the first medical device (e.g., IMD 14A) includes one or more sensors 40 to sense motion and/or respiration rate, and the information that the first medical device communicates to the second medical device includes information indicative of sensed motion and/or respiration rate. In some examples, the first medical device includes a microphone (e.g., a microphone is an example of one or more sensors 40) configured to sense trachea sounds associated with breathing or snoring of the patient 12, and the information that the first medical device communicates to the second medical device includes information indicative of the sensed trachea sounds.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure. Various examples are described herein, such as the following examples.

Example 1. A medical device for obstructive sleep apnea therapy, wherein the medical device is a first medical device implantable within a head or neck of a patient, and wherein the first medical device comprises: therapy delivery circuitry coupled to a first set of electrodes implantable proximate to a first hypoglossal nerve within a tongue of the patient and configured to deliver a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and sensing circuitry coupled to the first set of electrodes and configured to receive a second electrical stimulation signal, delivered to the second hypoglossal nerve by the second medical device, that includes information that the second medical device communicates to the first medical device.

Example 2. The medical device of example 1, wherein to include the information to communicate to the second medical device, the first medical device is configured to modulate the first electrical stimulation signal.

Example 3. The medical device of any of examples 1 and 2, wherein the first medical device is configured to demodulate the second electrical stimulation signal to retrieve the information that the second medical device communicates to the first medical device.

Example 4. The medical device of any of examples 1-3, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

Example 5. The medical device of any of examples 1-4, wherein the first medical device is implantable in the head of the patient behind a first ear of the patient, and the second medical device is implantable in the head of the patient behind a second ear of the patient.

Example 6. The medical device of any of examples 1-5, wherein the first medical device includes one or more sensors configured to sense at least one of motion or respiration rate, and wherein the information that the first medical device communicates to the second medical device includes information indicative of the sensed motion or respiration rate.

Example 7. The medical device of any of examples 1-6, wherein the first medical device includes a microphone configured to sense trachea sounds associated with at least one of breathing or snoring of the patient, and wherein the information that the first medical device communicates to the second medical device includes information indicative of the sensed trachea sounds.

Example 8. A system for obstructive sleep apnea therapy, the system comprising: a first set of electrodes implantable proximate to a first hypoglossal nerve within a tongue of a patient; a second set of electrodes implantable proximate a second hypoglossal nerve within the tongue of the patient; a first medical device implantable within a head or neck of the patient and coupled to the first set of electrodes; and a second medical device implantable within the head or neck of the patient and coupled to the second set of electrodes, wherein the first medical device is configured to deliver an electrical stimulation signal via one or more of the first set of electrodes to the first hypoglossal nerve that causes the tongue of the patient to advance and includes information to communicate to the second medical device, and wherein the second medical device is configured to receive the information included in the electrical stimulation signal delivered by the first medical device via sensing of the electrical stimulation signal by one or more electrodes of the second set of electrodes.

Example 9. The system of example 8, wherein the electrical stimulation signal is a first electrical stimulation signal, and the information is first information, wherein the second medical device is configured to deliver a second electrical stimulation signal via one or more of the second set of electrodes to the second hypoglossal nerve that causes the tongue of the patient to advance and includes second information to communicate to the first medical device, and wherein the first medical device is configured to receive the second information included in the second electrical stimulation signal delivered by the second medical device via sensing of the second electrical stimulation signal by one or more electrodes of the first set of electrodes.

Example 10. The system of any of examples 8 and 9, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

Example 11. The system of any of examples 8-10, wherein the first medical device is implantable in the head of the patient behind a first ear, and the second medical device is implantable in the head of the patient behind a second ear.

Example 12. The system of any of examples 8-11, wherein the first set of electrodes are formed as exposed coil or cable of a first lead, and the second set of electrodes are formed as exposed coil or cable of a second lead.

Example 13. The system of any of examples 8-12, wherein the first medical device includes one or more sensors configured to sense at least one of motion or respiration rate, and wherein the information that the first medical device communicates to the second medical device includes information indicative of the sensed motion or respiration rate.

Example 14. The system of any of examples 8-13, wherein the first medical device includes a microphone configured to sense trachea sounds associated with at least one of breathing or snoring of the patient, and wherein the information that the first medical device communicates to the second medical device includes information indicative of the sensed trachea sounds.

Example 15. A method for obstructive sleep apnea treatment, the method comprising: delivering, with a first medical device that is implantable within a head or neck of a patient and coupled to a first set of electrodes implantable proximate to a first hypoglossal nerve within a tongue of the patient, a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and receiving, with the first medical device, a second electrical stimulation signal, delivered to the second hypoglossal nerve by the second medical device, that includes information that the second medical device communicates to the first medical device.

Example 16. The method of example 15, further comprising modulating the first electrical stimulation signal to include the information to communicate to the second medical device.

Example 17. The method of any of examples 15 and 16, further comprising demodulating the second electrical stimulation signal to retrieve the information that the second medical device communicates to the first medical device.

Example 18. The method of any of examples 15-17, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

Example 19. The method of any of examples 15-18, wherein the first medical device includes one or more sensors configured to sense at least one of motion or respiration rate, and wherein the information that the first medical device communicates to the second medical device includes information indicative of the sensed motion or respiration rate.

Example 20. The method of any of examples 15-19, the first medical device includes a microphone configured to sense trachea sounds associated with at least one of breathing or snoring of the patient, and wherein the information that the first medical device communicates to the second medical device includes information indicative of the sensed trachea sounds.

Example 21. The method of any of examples 15-20, wherein the electrical stimulation signal is a first electrical stimulation signal, and the information is first information, the method further comprising: delivering, with the second medical device, a second electrical stimulation signal via one or more of the second set of electrodes to the second hypoglossal nerve that causes the tongue of the patient to advance and includes second information to communicate to the first medical device, and receiving, with the first medical device, the second information included in the second electrical stimulation signal delivered by the second medical device via sensing of the second electrical stimulation signal by one or more electrodes of the first set of electrodes.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A medical device for obstructive sleep apnea therapy, wherein the medical device is a first medical device implantable within a head or neck of a patient, and wherein the first medical device comprises:
    therapy delivery circuitry coupled to a first set of electrodes implantable proximate to a first hypoglossal nerve within a tongue of the patient and configured to deliver a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and
    sensing circuitry coupled to the first set of electrodes and configured to receive a second electrical stimulation signal, delivered to the second hypoglossal nerve by the second medical device, that includes information that the second medical device communicates to the first medical device.

2. The medical device of claim 1, wherein to include the information to communicate to the second medical device, the first medical device is configured to modulate the first electrical stimulation signal.

3. The medical device of claim 1, wherein the first medical device is configured to demodulate the second electrical stimulation signal to retrieve the information that the second medical device communicates to the first medical device.

4. The medical device of claim 1, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

5. The medical device of claim 1, wherein the first medical device is implantable in the head of the patient behind a first ear of the patient, and the second medical device is implantable in the head of the patient behind a second ear of the patient.

6. The medical device of claim 1, wherein the first medical device includes one or more sensors configured to sense at least one of motion or respiration rate, and wherein the information that the first medical device communicates to the second medical device includes information indicative of the sensed motion or respiration rate.

7. The medical device of claim 1, wherein the first medical device includes a microphone configured to sense trachea sounds associated with at least one of breathing or snoring of the patient, and wherein the information that the first medical device communicates to the second medical device includes information indicative of the sensed trachea sounds.

8. A system for obstructive sleep apnea therapy, the system comprising:
    a first set of electrodes implantable proximate to a first hypoglossal nerve within a tongue of a patient;
    a second set of electrodes implantable proximate a second hypoglossal nerve within the tongue of the patient;
    a first medical device implantable within a head or neck of the patient and coupled to the first set of electrodes; and
    a second medical device implantable within the head or neck of the patient and coupled to the second set of electrodes,
    wherein the first medical device is configured to deliver an electrical stimulation signal via one or more of the first set of electrodes to the first hypoglossal nerve that causes the tongue of the patient to advance and includes information to communicate to the second medical device, and
    wherein the second medical device is configured to receive the information included in the electrical stimulation signal delivered by the first medical device via sensing of the electrical stimulation signal by one or more electrodes of the second set of electrodes.

9. The system of claim 8, wherein the electrical stimulation signal is a first electrical stimulation signal, and the information is first information,
    wherein the second medical device is configured to deliver a second electrical stimulation signal via one or more of the second set of electrodes to the second hypoglossal nerve that causes the tongue of the patient to advance and includes second information to communicate to the first medical device, and
    wherein the first medical device is configured to receive the second information included in the second electrical stimulation signal delivered by the second medical device via sensing of the second electrical stimulation signal by one or more electrodes of the first set of electrodes.

10. The system of claim 8, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

11. The system of claim 8, wherein the first medical device is implantable in the head of the patient behind a first ear, and the second medical device is implantable in the head of the patient behind a second ear.

12. The system of claim 8, wherein the first set of electrodes are formed as exposed coil or cable of a first lead, and the second set of electrodes are formed as exposed coil or cable of a second lead.

13. The system of claim 8, wherein the first medical device includes one or more sensors configured to sense at least one of motion or respiration rate, and wherein the information that the first medical device communicates to the second medical device includes information indicative of the sensed motion or respiration rate.

14. The system of claim 8, wherein the first medical device includes a microphone configured to sense trachea sounds associated with at least one of breathing or snoring of the patient, and wherein the information that the first medical device communicates to the second medical device includes information indicative of the sensed trachea sounds.

15. A method for obstructive sleep apnea treatment, the method comprising:
    delivering, with a first medical device that is implantable within a head or neck of a patient and coupled to a first set of electrodes implantable proximate to a first hypoglossal nerve within a tongue of the patient, a first electrical stimulation signal to the first hypoglossal nerve that causes the tongue of the patient to advance and includes information to communicate to a second medical device implantable within the head or neck of the patient and coupled to a second set of electrodes implantable proximate to a second hypoglossal nerve within the tongue of the patient; and
    receiving, with the first medical device, a second electrical stimulation signal, delivered to the second hypoglossal nerve by the second medical device, that includes information that the second medical device communicates to the first medical device.

16. The method of claim 15, further comprising modulating the first electrical stimulation signal to include the information to communicate to the second medical device.

17. The method of claim 15, further comprising demodulating the second electrical stimulation signal to retrieve the information that the second medical device communicates to the first medical device.

18. The method of claim 15, wherein the information to communicate to the second medical device includes one or more of information for when to stimulate, information of at least one of an amplitude, pulse width, or frequency of an electrical stimulation signal that the second medical device is to output, information indicative of patient characteristics, and information indicative of changes to programs.

19. The method of claim 15, wherein the first medical device includes one or more sensors configured to sense at least one of motion or respiration rate, and wherein the information that the first medical device communicates to the second medical device includes information indicative of the sensed motion or respiration rate.

20. The method of claim 15, the first medical device includes a microphone configured to sense trachea sounds associated with at least one of breathing or snoring of the patient, and wherein the information that the first medical device communicates to the second medical device includes information indicative of the sensed trachea sounds.

21. The method of claim 15, wherein the electrical stimulation signal is a first electrical stimulation signal, and the information is first information, the method further comprising:
    delivering, with the second medical device, a second electrical stimulation signal via one or more of the second set of electrodes to the second hypoglossal nerve that causes the tongue of the patient to advance and includes second information to communicate to the first medical device, and
    receiving, with the first medical device, the second information included in the second electrical stimulation signal delivered by the second medical device via sensing of the second electrical stimulation signal by one or more electrodes of the first set of electrodes.

* * * * *